United States Patent [19]
Tichy

[11] Patent Number: 5,477,564
[45] Date of Patent: Dec. 26, 1995

[54] WIND NOISE REDUCING, EDDY CURRENT VENTILATED EARFOIL

[76] Inventor: James B. Tichy, P.O. Box 1308, Sausalito, Calif. 94966

[21] Appl. No.: 298,500

[22] Filed: Aug. 30, 1994

[51] Int. Cl.⁶ .................................................. A42B 3/16
[52] U.S. Cl. ........................... 2/423; 2/422; 2/425; 2/209
[58] Field of Search ................................ 2/421, 422, 423, 2/425, 410, 209, 175.6, 184.6, 909; 128/864, 866

[56] References Cited

U.S. PATENT DOCUMENTS

| | | |
|---|---|---|
| 437,602 | 9/1890 | Kaiser . |
| 1,768,068 | 11/1928 | Jauss . |
| 1,853,131 | 6/1931 | Lewis . |
| 2,140,630 | 12/1938 | Illguth ........................................ 2/423 |
| 2,537,201 | 11/1948 | Amfitheatrof . |
| 2,672,864 | 7/1951 | Makara . |
| 3,497,874 | 3/1970 | Molitoris . |
| 3,728,741 | 4/1973 | Lepor . |
| 4,344,425 | 8/1982 | Strauss . |
| 4,616,643 | 10/1986 | Jung . |
| 4,660,229 | 4/1987 | Harris . |
| 4,670,911 | 6/1987 | Dunford . |
| 4,682,374 | 7/1987 | Geiser . |
| 4,713,843 | 12/1987 | Duncan . |
| 4,791,684 | 12/1988 | Schwartz . |
| 5,086,789 | 2/1992 | Tichy . |
| 5,231,704 | 8/1993 | Hildenbrand . |
| 5,323,493 | 6/1994 | Ogiba ........................................ 2/422 |

OTHER PUBLICATIONS

Silencer ear covers, New York Design Studios, *Bicycling*, p. 30, May 1993.
Helmufs triangular ear covers, *Bicycling*, p. 30, Apr. 1994.
Journal of Sound and Vibration (1978) 58(2), pp. 285–291 "Experiments on the Noise Heard by Human Beings When Exposed to Atmospheric Winds", 1978 Academic Press Inc. (London) Ltd.
Evaluation of Fatigue & The Function of Maintaining Concentration, Eimatsu Takakuma 1982, Hokkaido Univ. Medical Lib. Series, vol. 14.
NASA Technical Papaer 2202, Kevin Shepherd, Jack Leatherwood, Sherman Clevenson, "Effect of Low–Frequency Tones and Turbulent–Boundary–Layer Noise on Annoyance", 1983.
Acoustical Factors Affecting Hearing Aid Performance, Gerald Studebaker, Univ. Park Press 1980, Chapter 6, The Acoustics of the External Ear, Edgar Shaw.
Journal of the Acoustical Society of America, vol. 18, No. 2, Oct. 1946, "The Pressure Distribution in the Auditory Canal in a Progressive Sound Field".

*Primary Examiner*—C. D. Crowder
*Assistant Examiner*—Michael A. Neas
*Attorney, Agent, or Firm*—Townsend and Townsend and Crew

[57] ABSTRACT

An earfoil (2) is used with a helmet (4) having a chin strap (6) which passes in front of the ear (30) and under the chin. The earfoil includes a wind deflecting, sound-permeable earfoil body (22) sized to cover the user's ear. The front edge (44) of the earfoil body is secured to the chin strap and lies against the user's head. The upper edge (46) of the earfoil body is secured to the lower circumferential edge (52) of the helmet just above the user's ear. These attachments are such that the earfoil body overlies the rear flange (56) of the user's ear while the rearward edge (62) of the earfoil body is spaced apart from the ear flange. This permits eddy current airflow to occur about the ear flange to enhance cooling even while the earfoil body directs airflow away from the concha (28) of the user's ear. The invention provides for a reduction in personally heard wind noise with enhanced eddy current cooling.

16 Claims, 3 Drawing Sheets

WIND NOISE REDUCING, EDDY CURRENT VENTILATED EARFOIL

CROSS-REFERENCE TO RELATED APPLICATIONS

This application is related to U.S. Pat. No. 5,086,789 issued Feb. 11, 1992, the disclosure of which is incorporated by reference.

BACKGROUND OF THE INVENTION

The present invention relates generally to wind deflector apparel. More particularly, it concerns a device for redirecting wind away from the ear for the purpose of decreasing any personally heard wind noise generated by air flow past the ear and head, while at the same time permitting ambient sound to pass substantially unattenuated through to the ear canal and permitting eddy current air flow about the ear flange to enhance cooling.

There are two main sources of perceived wind noise. In a head wind the first source is due to the shape of the head causing turbulence just behind the cheek bone, and is mainly responsible for the very low frequency noise. The second source appears to be due to stream flow by the concha which is the shallow cavity inside the ear just adjacent to the sensitive ear canal, and is apparently responsible for the higher frequency noise.

At low wind speeds, the combined noise spectrum creates a personal rumbling in the ear canal which gets louder and also higher in frequency as the wind speed increases. Unweighted measurements have been made of the noise created in the concha by the use of a microphone probe apparatus. See, U. R. Kristiansen, O.K.Ø. Pettersen 1978 *Journal of Sound and Vibration*, "Experiments On The Noise Heard By Human Beings When Exposed To Atmospheric Winds", 58(2)285–291. For an average person facing a 21 mile per hour (mph) wind the noise spectrum was found to extend below 25 cycles per second (Hz) to about 150 Hz at an intensity of 92 decibels (db) above quiet hearing threshold. The noise spectrum then tapers off in intensity to 60 db at 2400 Hz. Articulation tests have shown that the band of speech frequencies most important for intelligibility is that extending from about 500 to 2500 Hz. The signal to noise ratio of speech to wind induced ear canal noise can significantly deteriorate for winds above 20 mph. This comes as no surprise to hard of hearing sufferers who have lost their high frequency sensitivity and must completely rely on the lower part of the hearing spectrum. Even bike riders, sailors, skiers, etc. with good hearing may have considerable difficulty hearing ambient sounds such as traffic, conversation between companions, safety warnings and certain sounds of nature. High relative wind speeds are not uncommon, e.g., by bicycling 15 mph into a 15 mph atmospheric wind the relative headwind is 30 mph. Then too, for those who simply stand still on a windy day, such as pedestrians, construction workers and field workers, the same noise can be heard with additional low frequency pulses.

There is the additional problem of fatigue. The apparent intensity of the wind seems to be greater when it can also be heard. Constant and especially gusty wind noise over a long period of time can create considerable fatigue, which if not corrected can reduce the enjoyment of an activity and can even turn to irritation. Worse, fatigue can also be a contributing factor in creating misjudgments and accidents. Some children are quite susceptible to wind induced noise in the ear.

For the most part, this is a problem people have learned to live with. Mechanical devices such as ear plugs and ear muffs are designed to protect the ear against very loud machinery noises. By their very nature they are not completely sound permeable but contain a considerable amount of sound resistant material.

Heavy duty earmuffs, that are primarily designed to warm the ears, generally handle wind noise abatement as a secondary feature. For instance, Geiser, U.S. Pat. No. 4,582,374, provides for open ventilator holes drilled or cast through an otherwise solid, heat insulated protecting case. The uncovered holes are exposed to the windstream alongside the head (such as during skiing); and because they are open and uncovered to the outside, each hole becomes a wind noise generator. Such heavy duty earmuffs are uncomfortable to wear in the summer.

Simpler, more traditional ear cover paraphernalia include wool caps, flat earmuffs, and headbands which pass over and press on the ear flange. By necessity, they must be somewhat snug in order to keep out the wind. The popularity of these apparel notwithstanding, many people do not like their ears pressed against their heads and prefer to go without protection.

From an aeroacoustical standpoint, depending on the surface material used, headbands and caps are fairly efficient in eliminating mid and high frequency wind noise (the blowing sound "WH") because they divert the airflow past the external ear where that specific noise is generated. But the elimination of the low frequency rumble is elusive. Heavier materials are currently being used in some common earmuffs to address this problem but the ambient high frequency sound transmission to the ear is compromised. Ironically, it is the high frequencies that allow the external ear to sense fore and aft direction of the sound source accurately, an important safety feature on the work site.

Attempts at low frequency wind noise abatement are not new. In 1954, Hayes and Cudworth, published experimental data concerning a crude windscreen design which was tested at the Acoustics Laboratory, Massachusetts Institute of Technology, under contract with the Air Force. (J. R. M. Hayes and A. L. Cudworth (1954), letters to the editor "*Windscreen for the Ear*" J. Acoust. Soc. Am. 26, 254–5.) The windscreen was made up of two cylindrical cups, each 2¾" diameter by 3½" long (20 cubic inches each). The surface, made of woven nylon cloth with negligible ambient sound attenuation, was stretched over a ¼" mesh screen matrix. Standard earphone cushions and an earphone headband provided sealed contact with the head.

Partial results of the test show that at a wind speed of 20 mph, the windscreen attenuated the wind noise of the unprotected ear canal by an average of 21 decibels (dB) at 200 cycles per second (Hz), and 13 dB at around 500 Hz. This is a significant drop in noise level, especially at the lower frequency. However, people will likely not wear such unwieldy cylinders over their ears when they can use the less effective but much simpler headband.

Another problem with conventional noise abating earmuffs is that they substantially restrict the transfer of heat from the user's ear and the region of the user's head about the ear. In some cases the overheating of the user's ear can be so uncomfortable as to cause the user to remove the earmuffs and put up with the wind noise, with its attendant disadvantages, at least for a period of time.

SUMMARY OF THE INVENTION

The present invention is directed to a wind noise reducing, eddy current ventilated earfoil especially adapted for use with helmets or other headgear secured to the head with a chin strap, typically of the type that bicycle riders wear. The invention directs airflow past the concha of the user's ear while permitting ambient sound to be heard by the user and promoting eddy current airflow about the user's ear flange for effective cooling of the user's ear and head.

The earfoil is preferably used with a helmet of the type having a lower circumferential edge, a portion of which passes adjacent the upper edge of the user's ear. The helmet also has a chin strap extending from the helmet down past the front of the ear and under the chin. Typically the chin strap includes front and rear straps which connect to the helmet and pass in front of and behind the ear and connect at a common connection beneath the ear. Such a chin strap also has a lower strap connected to the common connection and extending beneath the user's jaw. The front and rear straps both preferably lie adjacent the user's head.

The earfoil includes a wind deflecting, soundpermeable earfoil body sized to cover the user's ear. The forward edge of the earfoil is secured to the forward strap, preferably so that the forward edge of the earfoil body lies against the user's head. The upper edge of the earfoil body is secured to the helmet, preferably to the circumferential edge of the helmet at a position overlying the user's ear. These attachments are such that the earfoil body overlies the ear flange of the user's ear while the earfoil body is spaced apart from the ear flange. This permits eddy current airflow to occur about the ear flange to enhance cooling even while the earfoil body directs airflow away from the concha of the user's ear to provide for a reduction in wind noise with enhanced eddy current cooling.

The earfoil body can be either permanently secured to one or both of the chin strap and helmet or, and more preferably, removably secured thereto. For stability it is preferred that the earfoil body be secured at what is or are effectively three points. One way of doing so is to secure the earfoil body along the length of the front strap and at a single point along the circumferential edge of the helmet. While hook and loop fasteners are preferred for removably securing the earfoil body to the helmet and to the chin strap, other types of removable fasteners, such as snaps, clips and hooks, could be used as well.

One advantage of using hook and loop fasteners, especially in connecting the earfoil body to the circumferential edge of the helmet, is the flexibility it provides. The front to back position along the helmet as well as the angle of attachment can be varied by the user to suit the particular circumstance. Repositioning the earfoil body is quite simple using such fastening elements.

Other features and advantages of the invention will appear from the following description in which the preferred embodiment has been set forth in detail in connection with the accompanying drawings.

DESCRIPTION OF THE PREFERRED EMBODIMENTS

Figure 1:
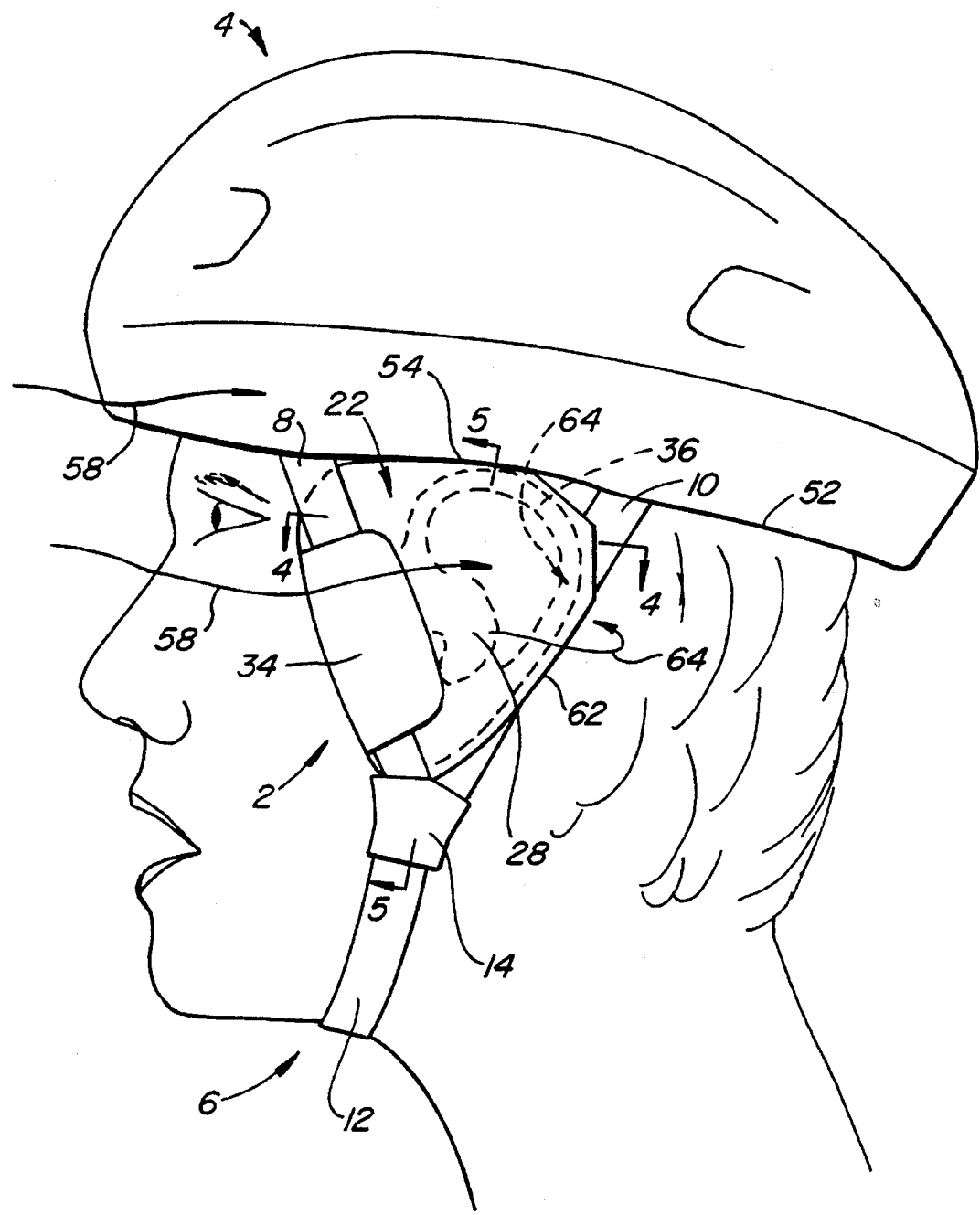
FIG. 1 is a side view showing an earfoil made according to the invention mounted to a helmet and worn by a user.
Figure 2:
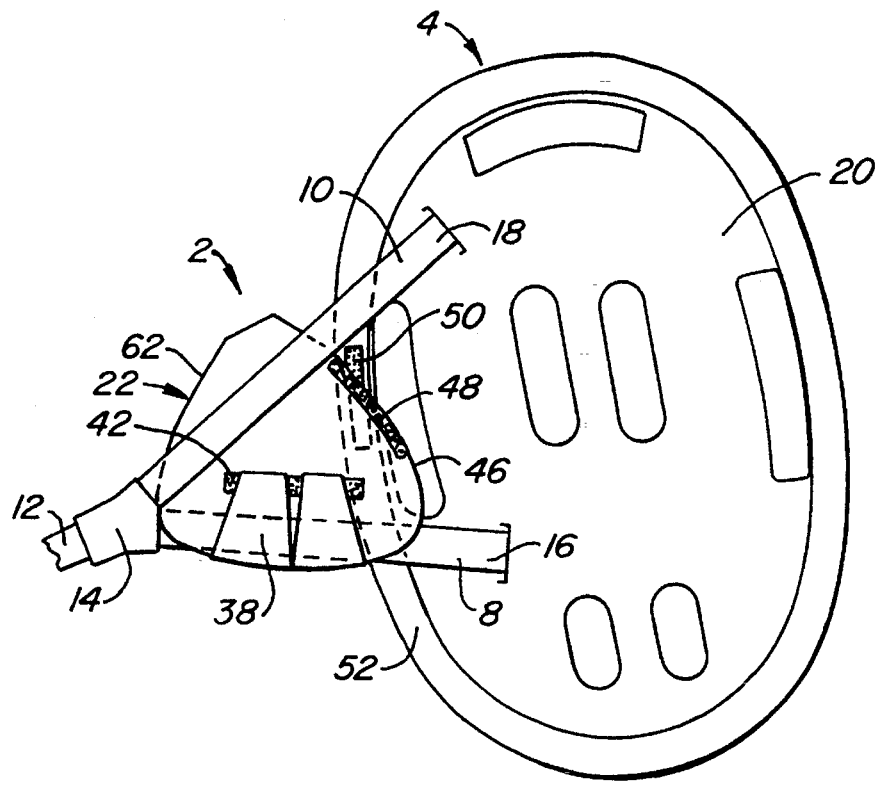
FIG. 2 is bottom plan view showing the helmet and one end of the chin strap extending laterally away from the helmet with an earfoil secured to the front strap and with the hook and loop fasteners, which normally secure the upper edge of the earfoil body to the circumferential edge of the helmet.

FIG. 1 illustrates an earfoil 2 mounted to a helmet 4 and a chin strap 6. Chin strap 6 includes a front strap 8, a rear strap 10 and a lower strap 12 secured to the front and rear straps at a common connection 14. The upper ends 16, 18 of front and rear straps 8, 10 are secured to and extend from the inside surface 20 of helmet 4 as is conventional; see FIG. 2.

Figure 4:
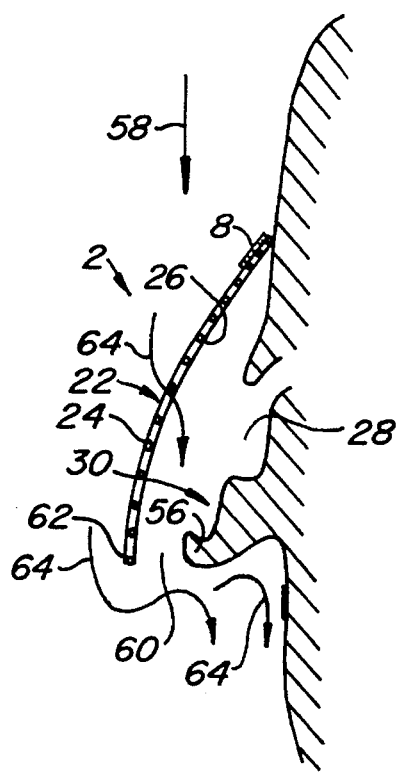
FIG. 4 is cross-sectional view taken along line 4—4 of FIG. 1 illustrating the convex cross-sectional shape of the earfoil body and eddy current airflow about the ear flange of the user.

Earfoil 2 includes an earfoil body 22 having a generally smoothly curving, convex shape as shown in FIG. 4. Body 22 includes a fabric outer cover 24 which covers a mesh framework 26. A material such as a single weave nylon Lycra Spandex or a single weave Georgette polyester provides a good sound permeable aeroacoustic boundary layer surface. The mesh framework 26 is cut from a commercially available thermoplastic acetate square mesh sheet composed of parallel filaments 0.022 inches thick and separated by 0.143 inches. The blank mesh forms are then thermoformed in a designed compound surface mold. This provides a comfortable, flexible yet form-holding rigidity which maintains the shape for earfoil 2.

Figure 3A:
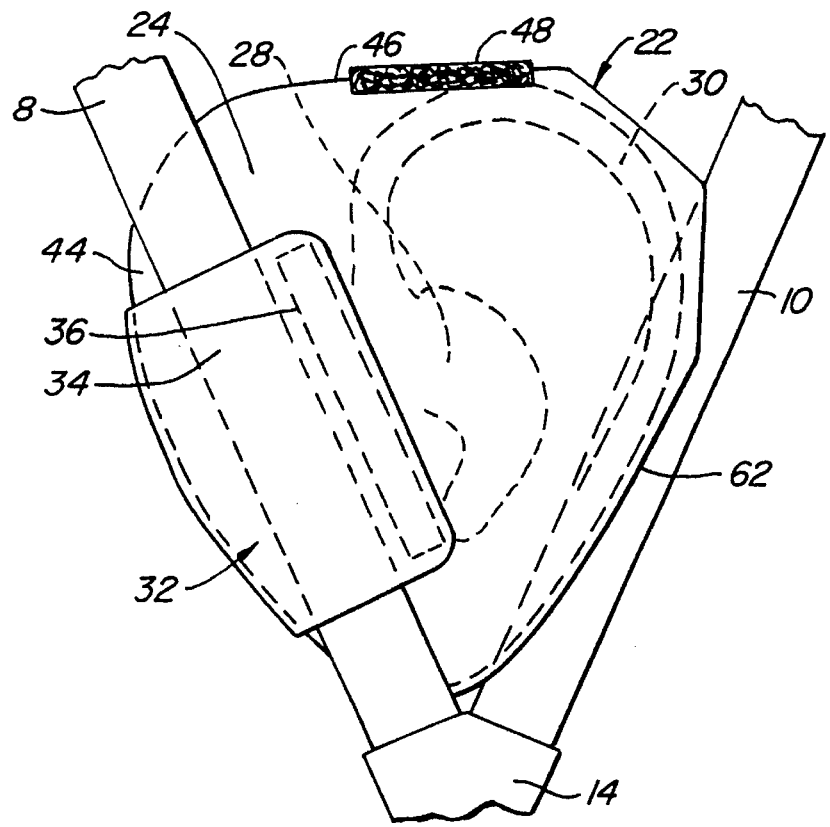
FIG. 3A is an enlarged view of the earfoil of FIG. 1 shown mounted to the chin strap but with the helmet removed.
Figure 3:
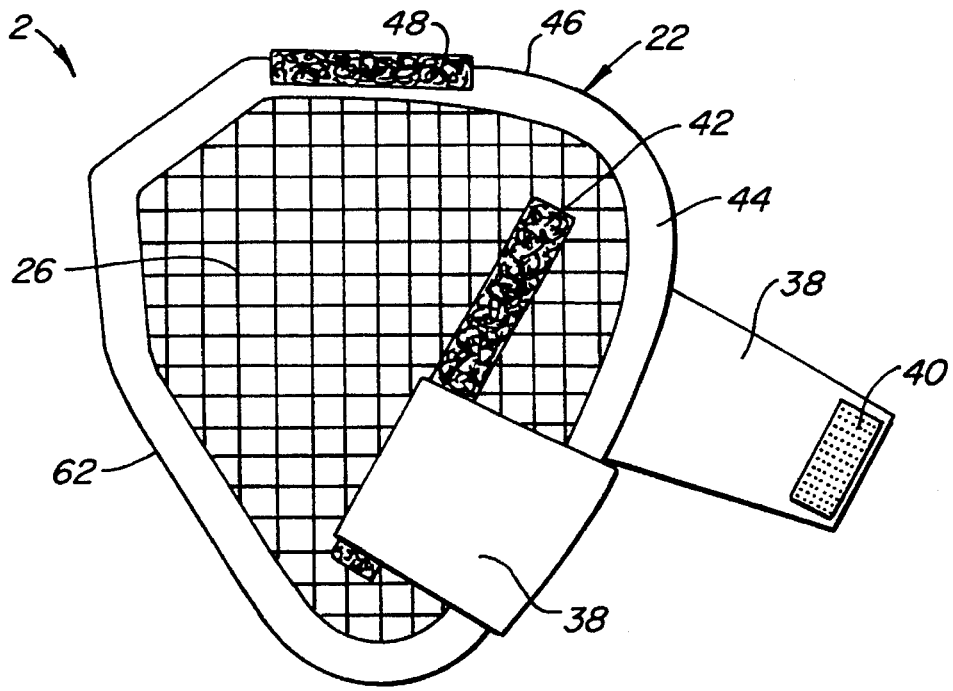
FIG. 3 is an enlarged inside view of the earfoil of FIG. 2 with one of the mounting straps in a secured position and the other mounting strap in an unsecured position.

FIG. 3A shows body 22 mounted to front strap 8 by mounting strap assembly 32. Mounting strap assembly includes a first part 34 which is glued and doubly sewn on to cover 24. This is shown by dashed lines 36 in FIG. 3A. Sewing in turn fastens the loop fastener 42 to the interior surface of 26 of earfoil body 22 as seen in FIG. 3. The external sewing makes a low aerodynamic profile to any airflow so that the attachment at 36 does not generate its own undesirable local noise pattern so close to the ear canal. First part 34 wraps over front strap 8 and captures the front strap between first part 34 and earfoil body 22. Strap 32 continues and splits into two mounting straps 38 each having strips of hook fasteners 40 at their distal ends. Hook fasteners 40 are used to secure the distal ends of mounting straps 38 to a loop fastener 42 mounted over mesh framework 26 of body 22. The extended length of strap assembly 32 along front strap 8 provides a great deal of stability in the mounting of the front edge 44 of earfoil body 22 to front strap 8.

Figure 5:
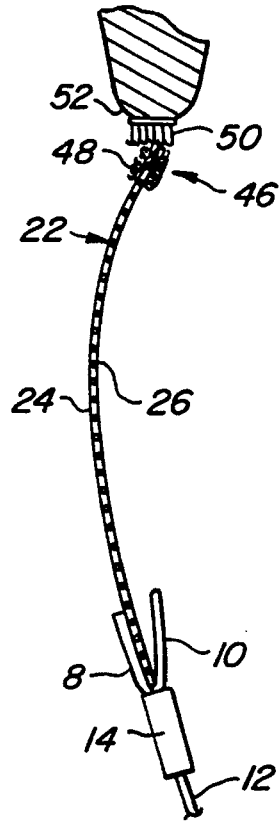
FIG. 5 is an enlarged cross-sectional view taken along line 5—5 of FIG. 1 illustrating the convex cross-sectional shape of the earfoil body and the attachment of the upper edge of the earfoil body to the lower circumferential edge of the helmet.

As seen in FIGS. 3, 3A and 5, the upper edge 46 of body 22 has a loop fastener strip 48 mounted thereto. Fastener strip 48 is positioned to engage a hook fastener strip 50 mounted along the lower circumferential edge 52 of helmet 4 at a position 54 between front and rear straps 8, 10. Position 54 is generally directly above ear 30 when helmet 4 is worn. The use of loop and hook fastener strips 48, 50 permit the user to securely fasten body 22 of earfoil 2 to the lower circumferential edge 52 of helmet 4 to the appropriate position and angular orientation to suit the user. By adjusting such placement, the distance body 22 of earfoil 2 is from the ear flange 56 (see FIG. 4) of ear 30, and thus the size of the enclosure formed by earfoil 2, can be varied. The aerodynamic angle of the earfoil with respect to the airflow 58 can be adjusted. Also, the eddy current opening 60 formed between the rearward edge 62 of body 22 and rear flange 56 of ear 30 can be adjusted. The provision for this eddy current air flow provides for cooling airflow about rear flange 56 of the user's ear 30 as indicated by arrows 64. As suggested in FIG. 1, eddy current air flow 64 can also occur from above upper edge 46 of body 22 and downwardly behind rear flange 56 of ear 30. These eddy currents do not however, create any significant air flow about the concha 28 of ear 30 and thus do not contribute to undesirable wind noise.

While the present invention can be made as a part of original equipment headgear, for example a bicycling helmet, it also has great utility as an aftermarket modification of a conventional bicycling helmet and chin strap assembly. In such a case, the user could simply mount a length of hook fastener strip 50 to lower circumferential edge 52 of helmet 4 and then wrap mounting straps 38 about front strap 8 to secure earfoil 2 to the front strap. The final position of earfoil body 22 can be adjusted through the engagement and disengagement of loop and hook fastener strips 48, 50 to achieve the desired front to back and side to side orientation and position of earfoil body 22. In some circumstances, such as when there is a strong side wind, the user may want to adjust the size of the eddy current opening 60 to account for such a circumstance. The present invention is designed to be very flexible in permitting the user to easily adapt it to an existing helmet and chin strap assembly and, once adapted, to easily and quickly make any adjustments necessary to the position and orientation of the earfoil for maximum effectiveness and comfort.

Modifications and variation can be made to disclosed embodiment without departing from the subject of the invention as defined in the following claims. For example, while the invention is particularly adaptable to helmet and chin strap assemblies including the Y-shaped chin strap shown in the figures, it can also be used with a straight chin strap which passes forward of the user's ear. Also, upper edge 46 of body 22 could be secured to positions on helmet 4 other than circumferential edge 52; for example, upper edge 46 of body 22 could be secured to a flexible strap or a rigid or semi-rigid member extending from helmet 4. Also, loop fastening strips could be mounted to the outside of earfoil body 22 near its upper edge 46 and to the outside of helmet 4 above the ear; a separate hook fastening strip could then be used to fasten earfoil body 22 to helmet 4. Alternatively, body 22 could be indirectly secured to helmet by securing upper edge 46 to a supplemental strap secured at either end to front and rear straps 8, 10.

What is claimed is:

1. A wind noise reducing earfoil kit for use with headgear of the type having a portion which passes adjacent the upper edge of a user's ear, the helmet also having a chin strap, the chin strap extending from the headgear downwardly in front of the user's ear and beneath the user's jaw, the kit comprising:

a wind-deflecting, sound-permeable earfoil body sized to cover the user's ear, the earfoil body including a forward edge and a rearward edge;

a first attachment assembly for securing the earfoil body to the chin strap so the forward edge of the earfoil body lies against the user's head; and a second attachment assembly for securing the earfoil body to the headgear so to position the earfoil body overlying the ear flange of the ear and the rearward edge of the earfoil body spaced apart from the ear flange of the ear to create a rearwardly facing eddy current opening therebetween;

whereby eddy current air flow can occur about the ear flange so to enhance cooling as the earfoil body directs air flow away from the concha of the user's ear.

2. The kit of claim 1 wherein the second attachment assembly is an adjustable position attachment assembly.

3. The kit of claim 1 wherein earfoil body includes an upper edge and the second attachment assembly secures the upper edge to the headgear.

4. The kit of claim 1 wherein the second attachment assembly secures the earfoil body directly to the headgear.

5. The kit of claim 1 wherein the earfoil body includes an inner screen covered by a fabric.

6. The kit of claim 1 wherein the earfoil body has a generally convex outer surface.

7. The kit of claim 1 wherein the first attachment assembly includes a hook and loop fastener system including a length of fabric which wraps around the chin strap.

8. An improved helmet of the type having a lower circumferential edge a portion of which passes adjacent the upper edge of a user's ear, the helmet also having a chin strap including front and rear straps, extending from the lower circumferential edge of the helmet on the lateral sides of the helmet downwardly to a common connection beneath the ear, and a lower strap connecting to the common connection and extending beneath the user's jaw, the front and rear straps positioned to lie forward and rearward of the concha of the user's ear, the improvement comprising:

a wind-deflecting, sound-permeable earfoil body sized to cover the user's ear, the earfoil body including a forward edge and a rearward edge;

a first attachment assembly securing the earfoil body to the chin strap so the forward edge of the earfoil body lies against the user's head; and a second attachment assembly securing the earfoil body to the portion of the circumferential edge of the helmet so to position the earfoil body overlying the ear flange of the ear and the rearward edge of the earfoil body spaced apart from the ear flange of the ear to create a rearwardly facing eddy current opening therebetween;

whereby eddy current air flow can occur about the ear flange so to enhance cooling as the earfoil body directs air flow away from the concha of the user's ear.

9. The improvement of claim 8 wherein the second attachment assembly includes a first attachment element secured to the portion of the circumferential edge of the helmet and a second attachment element, which engages with the first attachment element, secured to the upper edge of the earfoil body.

10. The improvement of claim 9 wherein the first and second attachment elements include hook and loop fastener elements.

11. A wind noise reducing earfoil kit for use with a helmet of the type having a lower circumferential edge a portion of which passes adjacent the upper edge of a user's ear, the helmet also having a chin strap including front and rear straps, extending from the lower circumferential edge of the helmet on the lateral sides of the helmet downwardly to a common connection beneath the ear, and a lower strap connecting to the common connection and extending beneath the user's jaw, the front and rear straps positioned to lie forward and rearward of the concha of the user's ear, the kit comprising:

a wind-deflecting, sound-permeable earfoil body sized to cover the user's ear, the earfoil body including an upper edge, a forward edge and a rearward edge;

a first attachment assembly adjustably securing the earfoil body to the forward strap so the forward edge of the earfoil body lies against the user's head; and a second attachment assembly including a first hook and loop attachment element secured to the portion of the circumferential edge of the helmet and a second hook and loop attachment element, engageable with the first hook and loop attachment element, secured to the upper edge of the earfoil body, the second attachment assembly adjustably securing the upper edge of the earfoil body to the portion of the circumferential edge of the helmet so to position the earfoil body overlying the ear flange of the ear and the rearward edge of the earfoil body spaced apart from the ear flange of the ear to create a rearwardly facing eddy current opening between the earfoil body and the ear flange;

whereby eddy current air flow can occur about the ear flange so to enhance cooling as the earfoil body directs air flow away from the concha of the user's ear.

12. A method for modifying a helmet of the type having a chin strap extending downwardly from the helmet, in front of the user's ear and beneath the user's jaw, comprising the following steps:

selecting a wind-deflecting, sound-permeable earfoil body sized to cover the user's ear; and securing the earfoil body to overlie the ear flange with the earfoil body spaced apart from the ear flange to create a rearwardly facing eddy current opening between the earfoil body and the ear flange by:
 (a) securing the earfoil body to the chin strap so a forward edge of the earfoil body lies adjacent to the user's head; and
 (b) securing the earfoil body to the helmet;

whereby eddy current air flow can occur about the ear flange so to enhance cooling as the earfoil body directs air flow away from the concha of the user's ear.

13. The method of claim 12 wherein the selecting step is carried out by selecting an earfoil body having a convex outer surface.

14. The method of claim 12 wherein the (a) securing step includes the step of positioning the forward edge of the earfoil body between the strap and the user's head.

15. The method of claim 12 wherein the (b) securing step is carried out using hook and loop fastener elements.

16. A method for modifying a helmet of the type having a lower circumferential edge a portion of which passes adjacent to the upper edge of a user's ear, the helmet also having a chin strap including front and rear straps, extending from the circumferential edge of the helmet on the lateral sides of the helmet downwardly to a common connection beneath the ear, and a lower strap connecting to the common connection and extending beneath the user's jaw, the front and rear straps positioned to lie forward and rearward of the concha of the user's ear, comprising the following steps:

selecting a wind-deflecting, sound-permeable earfoil body sized to cover the user's ear; and securing the earfoil body to overlie the ear flange with a rearward edge of the earfoil body spaced apart from the ear flange to create a rearwardly facing eddy current opening between the earfoil body and the ear flange by:
 securing a forward edge of the earfoil body to the forward strap so the forward edge of the earfoil body lies adjacent to the user's head; and
 adjustably securing an upper edge of the earfoil body to the portion of the circumferential edge of the helmet;

whereby eddy current air flow can occur about the ear flange so to enhance cooling as the earfoil body directs air flow away from the concha of the user's ear.

* * * * *